(12) United States Patent
Warne et al.

(10) Patent No.: US 7,758,860 B2
(45) Date of Patent: Jul. 20, 2010

(54) PROTEIN FORMULATIONS WITH REDUCED VISCOSITY AND USES THEREOF

(75) Inventors: Nicholas W. Warne, Andover, MA (US); Pilarin Elizabeth Louise Nichols, Andover, MA (US); Paulo J. Loureiro, Lawrence, MA (US)

(73) Assignee: Wyeth LLC, Madison, NJ (US)

( * ) Notice: Subject to any disclaimer, the term of this patent is extended or adjusted under 35 U.S.C. 154(b) by 321 days.

(21) Appl. No.: 12/031,307

(22) Filed: Feb. 14, 2008

(65) Prior Publication Data

US 2008/0160014 A1 Jul. 3, 2008

Related U.S. Application Data

(62) Division of application No. 11/644,079, filed on Dec. 21, 2006, now Pat. No. 7,390,786.

(60) Provisional application No. 60/752,660, filed on Dec. 21, 2005.

(51) Int. Cl.
*A61K 38/395* (2006.01)
(52) U.S. Cl. .................................................. 424/138.1
(58) Field of Classification Search ................ 424/138.1
See application file for complete search history.

(56) References Cited

U.S. PATENT DOCUMENTS

| 6,267,958 | B1 | 7/2001 | Andya et al. |
| 6,858,208 | B2 | 2/2005 | Lee et al. |
| 6,875,432 | B2 | 4/2005 | Liu et al. |
| 6,914,128 | B1 | 7/2005 | Salfeld et al. |
| 2002/0045571 | A1 | 4/2002 | Liu et al. |
| 2003/0113316 | A1 | 6/2003 | Kaisheva et al. |
| 2004/0037893 | A1 | 2/2004 | Hansen et al. |
| 2004/0142382 | A1 | 7/2004 | Veldman et al. |
| 2004/0197324 | A1 | 10/2004 | Liu et al. |
| 2005/0107594 | A1 | 5/2005 | Sun et al. |
| 2005/0119172 | A1 | 6/2005 | Merkle |
| 2005/0175603 | A1 | 8/2005 | Liu et al. |
| 2006/0063228 | A1 | 3/2006 | Kasaian et al. |
| 2007/0212346 | A1 | 9/2007 | Igawa et al. |

FOREIGN PATENT DOCUMENTS

| EP | 1 688 432 | 8/2006 |
| WO | WO-02/30463 | 4/2002 |
| WO | WO-02/096457 | 12/2002 |
| WO | WO-2005-035574 | 4/2005 |
| WO | WO-2006/116269 | 11/2006 |

OTHER PUBLICATIONS

Liu, et al., "Reversible Self-Association Increases the Viscosity of a Concentrated Monoclonal Antibody in Aqueous Solution", Journal of Pharmaceutical Sciences, 94(9):1928-1940 (2005).
International Search Report and Written Opinion issued for PCT/US2006/049129, dated Feb. 26, 2008.

*Primary Examiner*—Maryam Monshipouri

(57) ABSTRACT

Protein formulations and methods for reducing the viscosity of a protein formulation are provided. The method for reducing the viscosity of a protein formulation comprises adding a viscosity reducing agent, such as calcium chloride or magnesium chloride to the protein formulation.

19 Claims, 8 Drawing Sheets

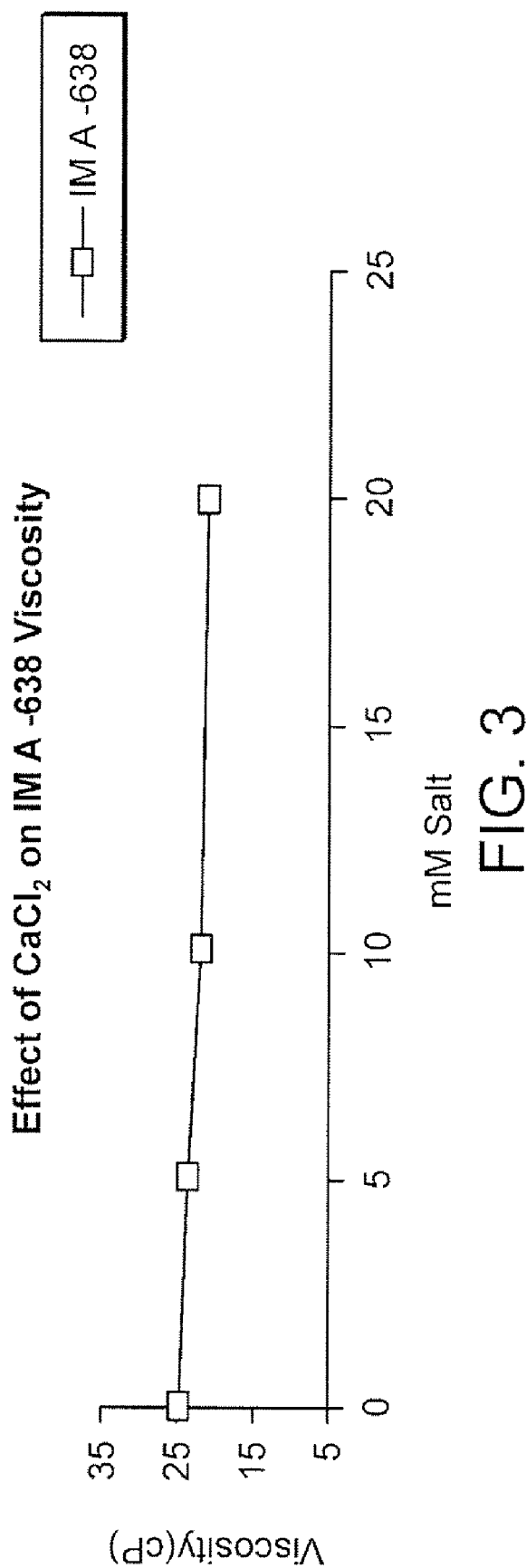

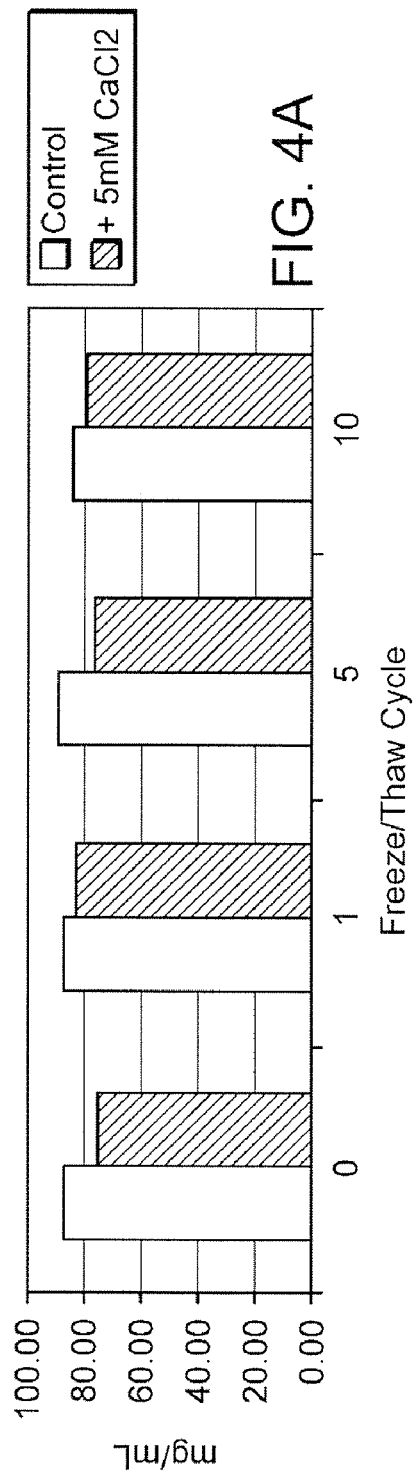
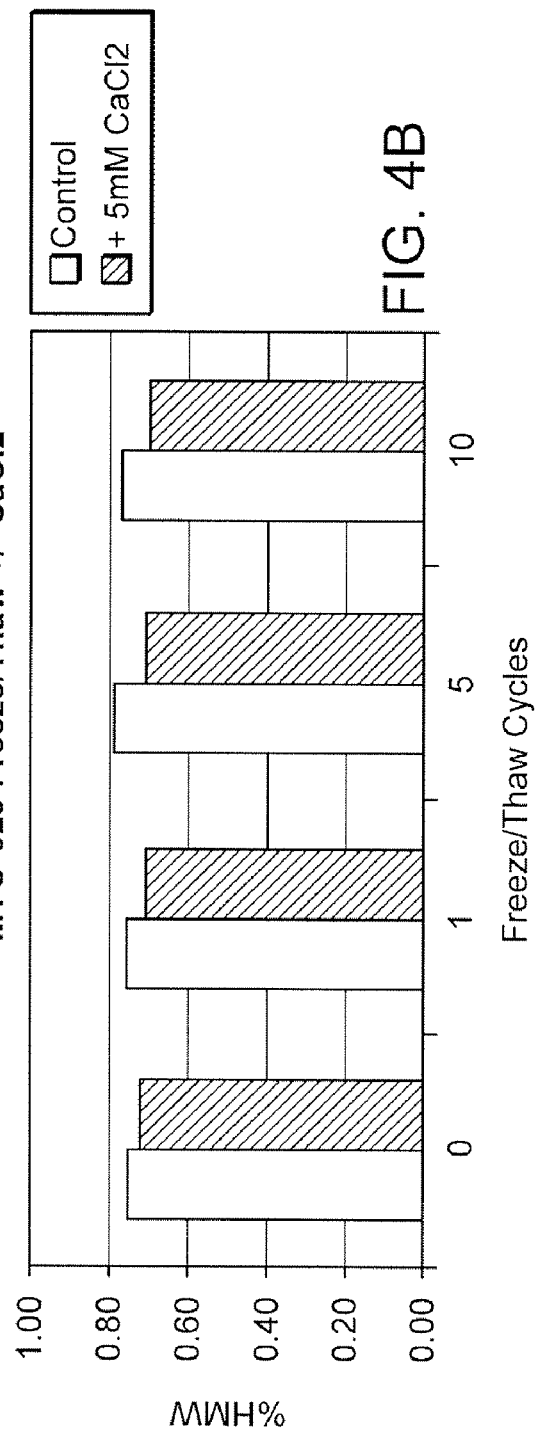
FIG. 4A
FIG. 4B

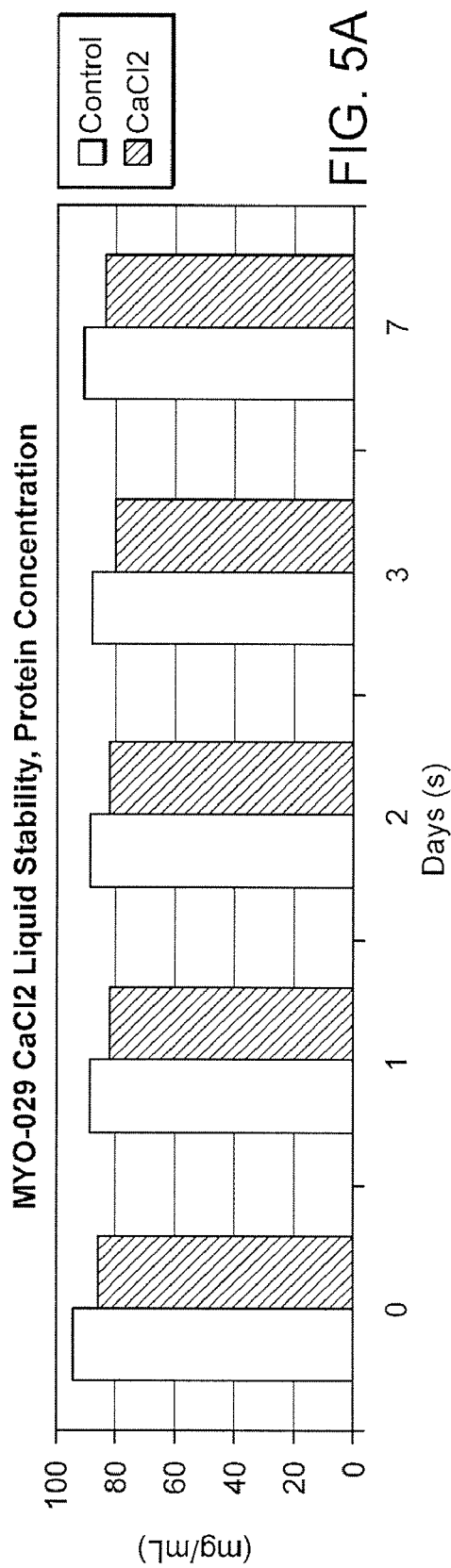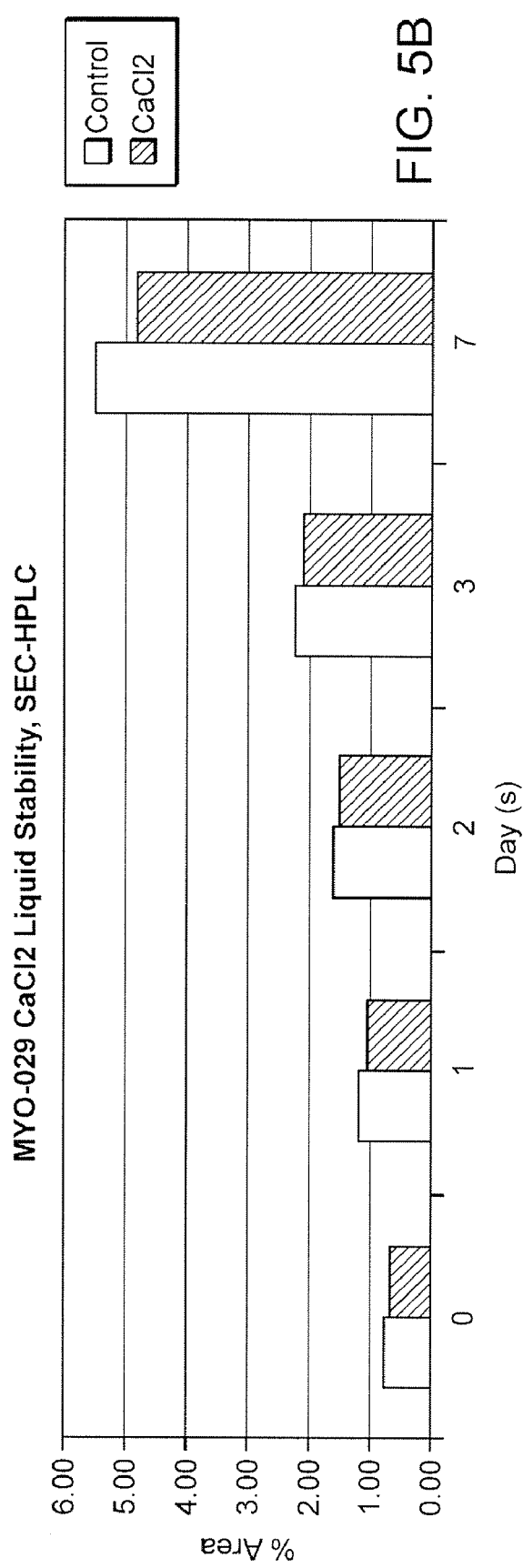

Amino acid sequences of Myo 28 IgG1/λ

Myo 28 Heavy Chain (based on DP47)

eVqLIESGGGLVQPGGSLRLSCAASGFTFSRYVINWVRQAPGKGLEWVSAISVTGGST
AYADSVRGRFTISRDNSKNTLYLQMNSLRAEDTAVYYCaKGQWERGSYYFDYWGRG
TLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK    (SEQ ID NO:1)

Myo 28 Light Chain (based on DPL8)

QSVLTQPPSVSGAPGQRVTISCTGSSNIGDGDGYDVHWYQQLPGTAPKLLIYGNSHRPS
GVPDRFSGSKSgTSASLAITGLQaEDEADYyCHSYDGSVSGWIFGGGTKLTVLGQPKA
APSVTLFPPSSEELQANKATLVCLISDFYPGAVTVAWKADSSPVKAGVETTTPSKQSNNK
YAASSYLSLTPEQWKSHRSYSCQVTHEGSTVEKTVAPTECS    (SEQ ID NO:2)

Variable regions are in bold
CDRs are in bold, italicized and underlined
Mutations introduced during germlining are in lower case and underlined
Constant regions are underlined.

FIG. 6

Myo 29 Heavy Chain (IgG1) (bold: VH; underlined: IgG1 human constant region)

QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARDENWG FDPWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKKA EPKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALHNHYTQ KSLSLSPGK (SEQ ID NO:3)

Myo 29 Light Chain (bold: VL; underlined: human lambda constant region)

SYELTQPPSVSVSPGQTASITCSGHALGDKFVSWYQQkpGQSPVLVIYDDTQRPS GIPeRFSGSNSGNTATLTISGTQAMDEADYyCQAWDSSFVFGGGTKVTVLGQPKAAPSVTLFPPSSEELQANKATLVCLISDFYPGAVTVAWKADSSPVKAGVETTTPSKQ SNNKYAASSYLSLTPEQWKSHRSYSCQVTHEGSTVEKTVAPTECS (SEQ ID NO:4)

Note: underlined lower case residues were changed in Myo 29 light chain to make it germ-line.

FIG. 7

Amino Acid Sequences of J695 Light and Heavy Chains

J695 Heavy chain (bold: Variable Region Sequences; underlined: IgG1 human constant region)

**QVQLVESGGGVVQPGRSLRLSCAASGFTFSSYGMHWVRQAPGKGLEWVAFIRYDGS
NKYYADSVKGRFTISRDNSKNTLYLQMNSLRAEDTAVYYCKTHGSHDNWGQGTMV
TVSS**ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO:5)

J695 Light chain (bold: Variable Region Sequences; underlined: human λ constant region)

**QSVLTQPPSVSGAPGQRVTISCSGSRSNIGSNTVKWYQQLPGTAPKLLIYYNDQRPS
GVPDRFSGSKSGTSASLAITGLQAEDEADYYCQSYDRYTHPALLFGTGTKVTVLGG**
QPKAAPSVTLFPPSSEELQANKATLVCLISDFYPGAVTVAWKADSSPVKAGVETTPSK
QSNNKYAASSYLSLTPEQWKSHRSYSCQVTHEGSTVEKTVAPTECS (SEQ ID NO:6)

FIG. 8

Predicted Amino Acid sequences of IMA-638 Light and Heavy Chains

Heavy Chain
EVQLVESGGGLVQPGGSLRLSCAASGFTFISYAMSWVRQAPGKGLEWVASISSGGNTYYPDSVKGRFTIS
RDNAKNSLYLQMNSLRAEDTAVYYCARLDGYYFGFAYWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPE<u>A</u>LG<u>A</u>PSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK   (SEQ ID NO:7)

Light Chain
DIQMTQSPSSLSASVGDRVTITCKASESVDNYGKSLMHWYQQKPGKAPKLLIYRASNLESGVPSRFSGSG
SGTDFTLTISSLQPEDFATYYCQQSNEDPWTFGGGTKVEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSSPVT
KSFNRGEC   (SEQ ID NO:8)

The two mutated residues to lower Fc effector function are indicated by an underline and the N-linked glycosylation consensus sequence is indicated by bold text.

SEQUENCE LISTING

<160> NUMBER OF SEQ ID NOS: 8

<210> SEQ ID NO 1
<211> LENGTH: 451
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

```
Glu Val Gln Leu Ile Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Val Ile Asn Trp Val Arg Gln Ala Pro Gly Lys Gly Leu Glu Trp Val
        35                  40                  45

Ser Ala Ile Ser Val Thr Gly Gly Ser Thr Ala Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gln Trp Glu Arg Gly Ser Tyr Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Cys Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 217
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Asp Gly
            20                  25                  30

Tyr Asp Val His Trp Tyr Gln Gln Leu Pro Gly Thr Ala Pro Lys Leu
        35                  40                  45

Leu Ile Tyr Gly Asn Ser His Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys His Ser Tyr Asp Gly Ser
                85                  90                  95

Val Ser Gly Trp Ile Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
```

-continued

```
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215

<210> SEQ ID NO 3
<211> LENGTH: 447
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Thr Ser Tyr
             20                  25                  30
Tyr Met His Trp Val Arg Gln Ala Pro Gly Gln Gly Leu Glu Trp Met
         35                  40                  45
Gly Ile Ile Asn Pro Ser Gly Gly Ser Thr Ser Tyr Ala Gln Lys Phe
     50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Asp Glu Asn Trp Gly Phe Asp Pro Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Glu Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Ala Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
```

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 4
<211> LENGTH: 211
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Ser Tyr Glu Leu Thr Gln Pro Pro Ser Val Ser Val Ser Pro Gly Gln
1               5                   10                  15

Thr Ala Ser Ile Thr Cys Ser Gly His Ala Leu Gly Asp Lys Phe Val
            20                  25                  30

Ser Trp Tyr Gln Gln Lys Pro Gly Gln Ser Pro Val Leu Val Ile Tyr
        35                  40                  45

Asp Asp Thr Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Phe Val Phe
                85                  90                  95

Gly Gly Gly Thr Lys Val Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210

-continued

```
<210> SEQ ID NO 5
<211> LENGTH: 445
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Lys Thr His Gly Ser His Asp Asn Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
```

```
                355                 360                 365
Gly Phe Tyr Pro Ser Asp Ile Ala Val Glu Trp Glu Ser Asn Gly Gln
            370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 6
<211> LENGTH: 218
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Gln Ser Val Leu Thr Gln Pro Pro Ser Val Ser Gly Ala Pro Gly Gln
  1               5                  10                  15

Arg Val Thr Ile Ser Cys Ser Gly Ser Arg Ser Asn Ile Gly Ser Asn
                 20                  25                  30

Thr Val Lys Trp Tyr Gln Gln Leu Pro Gly Thr Ala Pro Lys Leu Leu
             35                  40                  45

Ile Tyr Tyr Asn Asp Gln Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Gln Ser Tyr Asp Arg Tyr Thr
                 85                  90                  95

His Pro Ala Leu Leu Phe Gly Thr Gly Thr Lys Val Thr Val Leu Gly
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 7
<211> LENGTH: 448
<212> TYPE: PRT
<213> ORGANISM: Artificial Sequence
<220> FEATURE:
<223> OTHER INFORMATION: Description of Artificial Sequence: Synthetic
      construct
```

<400> SEQUENCE: 7

```
Glu Val Gln Leu Val Glu Ser Gly Gly Leu Val Gln Pro Gly Gly
  1               5                  10                  15

Ser Leu Arg Leu Ser Cys Ala Ala Ser Gly Phe Thr Phe Ile Ser Tyr
             20                  25                  30

Ala Met Ser Trp Val Arg Gln Ala Pro Gly Lys Gly Leu Glu Trp Val
         35                  40                  45

Ala Ser Ile Ser Ser Gly Gly Asn Thr Tyr Tyr Pro Asp Ser Val Lys
     50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Leu Asp Gly Tyr Tyr Phe Gly Phe Ala Tyr Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Leu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 8
<211> LENGTH: 218
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Ser Val Asp Asn Tyr
            20                  25                  30

Gly Lys Ser Leu Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215
```

PROTEIN FORMULATIONS WITH REDUCED VISCOSITY AND USES THEREOF

CROSS-REFERENCE TO RELATED APPLICATIONS

This application claims priority to U.S. application Ser. No. 11/644,079, filed on Dec. 21, 2006, which claims priority to U.S. Provisional Application No. 60/752,660, filed on Dec. 21, 2005, the contents of both of which are herein incorporated by reference in their entirety.

TECHNICAL FIELD

The field relates to protein formulations and, more particularly, to protein formulations with reduced viscosity.

BACKGROUND

It is estimated that more than 371 new biotechnology-based medicines are in the industry pipeline. Such biotechnology-based medicines include therapeutic proteins such as enzymes, soluble receptors, ligands, blood proteins, and monoclonal antibodies. Protein-based therapy, especially monoclonal antibody-based therapy, has become an important method for treating diseases such as cancer, allergic diseases, asthma, and organ transplantation. At the end of 2003 fourteen antibody-based therapies had been approved by the Food and Drug Administration to treat different human diseases.

Antibody-based therapy is usually administered on a regular basis and requires several mg/kg dosing by injection. Subcutaneous injection is a typical route of administration of these therapies. Because of the small volumes used for subcutaneous injection (usually 1.0 mL-1.2 mL), for high dose antibody therapies, this route of administration requires high concentration protein formulations (e.g., 50 mg/ml-300 mg/ml).

High protein concentrations pose challenges relating to the physical and chemical stability of the protein, and difficulty with manufacture, storage, and delivery of the protein formulation. One problem is the tendency of proteins to form particulates during processing and/or storage, which make manipulation during further processing difficult. To attempt to obviate this problem, surfactants and/or sugars have been added to protein formulations. Although surfactants and sugars may reduce the degree of particulate formation of proteins, they do not address another problem associated with manipulating and administering concentrated protein formulations, i.e., increased viscosity. In fact, sugars may enhance the intermolecular interactions within a protein or between proteins and increase the viscosity of the protein formulation.

Increased viscosity of protein formulations has negative ramifications from processing through drug delivery to the patient. Accordingly, there is a need in the art to develop relatively high concentration protein formulations with suitably low viscosities that are suitable for manufacture, storage, and administration.

SUMMARY

The instant application relates to protein formulations having reduced viscosity compared to a corresponding protein formulation that does not include a viscosity-reducing agent in a suitable concentration, and methods of making such protein formulations having reduced viscosity (reduced viscosity formulations).

In one aspect, the invention relates to methods of reducing the viscosity of a protein formulation by adding a viscosity reducing agent to a protein formulation, thereby reducing the viscosity of the protein formulation compared to a protein formulation lacking the viscosity reducing agent. In one embodiment, the method involves determining the viscosity of a protein formulation prior to the addition of a viscosity reducing agent. In another embodiment, the method involves determining the viscosity of a protein formulation after the addition of a viscosity reducing agent. In yet another embodiment, the method involves determining the viscosity of a protein formulation prior to and after the addition of a viscosity reducing agent. In certain embodiments, the viscosity reducing agent reduces the viscosity of the protein formulation by at least 5% compared to the viscosity of the formulation formulated without the viscosity reducing agent.

In some embodiments, the viscosity reducing agent is calcium chloride or magnesium chloride. The viscosity reducing agent is added at low concentrations so as not to negatively impact the protein formulation. The viscosity reducing agent is generally added to a protein formulation to a final concentration of between about 1 mM and about 50 mM. In some embodiments, the viscosity reducing agent is added to a protein formulation to a final concentration of between about 5 mM and about 25 mM. In certain embodiments, the viscosity reducing agent is added to a protein formulation to a final concentration of between about 1 mM and about 20 mM. In certain embodiments, the viscosity reducing agent is added to a protein formulation to a final concentration of between 0.5 mM and 14 mM. In another embodiment, the protein is an antibody, an Ig fusion protein, a receptor, a ligand, a transcription factor, an enzyme, or a biologically active fragment thereof. In some embodiments, the protein is an anti-myostatin antibody, an anti-IL-12 antibody, or an anti-IL-13 antibody.

In another aspect, the invention relates to a reduced viscosity protein formulation. The reduced viscosity protein formulation includes a protein, a viscosity reducing agent, and a buffer. In some embodiments, the viscosity reducing agent is calcium chloride or magnesium chloride. The viscosity reducing agent is generally added to a protein formulation to a final concentration of between about 1 mM and about 50 mM. In some embodiments, the viscosity reducing agent is added to a protein formulation to a final concentration of between about 5 mM and about 25 mM. In certain embodiments, the viscosity reducing agent is added to a protein formulation to a final concentration of between about 1 mM and about 15 mM. In certain other embodiments, the viscosity reducing agent is added to a protein formulation to a final concentration of between 0.5 mM and 14 mM. When the viscosity reducing agent is added to a protein formulation to a concentration of between about 0.5 mM to about 50 mM, sodium chloride and sodium biphosphate are not used as viscosity reducing agents. The pH of the protein formulation is generally between about 5.5 and about 6.5. In certain embodiments, the protein is an antibody, an Ig fusion protein, a receptor, a ligand, a transcription factor, an enzyme, or a biologically active fragment thereof. In certain embodiments, the protein formulations are provided as kits. Such kits can include instructions for use of the protein formulation.

In certain embodiments, the reduced viscosity protein formulation is a reduced viscosity anti-myostatin antibody formulation. In one embodiment, the anti-myostatin antibody is a monoclonal antibody. In another embodiment, the anti-myostatin antibody is a humanized monoclonal antibody (e.g., a partially humanized or fully humanized monoclonal antibody). In certain embodiments, the anti-myostatin antibody is MYO-022, MYO-028 or MYO-029. Anti-myostatin antibodies are generally used at a concentration of between about 25 mg/ml to about 400 mg/ml. The viscosity reducing agent is generally added to a reduced viscosity anti-myostatin antibody formulation to a final concentration of between about 1 mM and about 50 mM. In some embodiments, the viscosity reducing agent is added to an anti-myostatin antibody to a final concentration of between about 5 mM and about 25 mM. In certain embodiments, the viscosity reducing agent is added to an anti-myostatin antibody formulation to a final concentration of between about 1 mM and about 15 mM. In certain embodiments, the viscosity reducing agent is added to an anti-myostatin antibody formulation to a final concentration of between 0.5 mM and 14 mM. When the viscosity reducing agent is added to an anti-myostatin antibody formulation to a concentration of between about 0.5 mM to about 50 mM, sodium chloride and sodium biphosphate are not used as viscosity reducing agents. Reduced viscosity anti-myostatin antibody formulations generally have a pH of between about 5.5 and about 6.5. In one embodiment, histidine is used to buffer a reduced viscosity myostatin antibody formulation. A reduced viscosity myostatin antibody formulation can also include one or more cryoprotectants, one or more surfactants, one or more anti-oxidants, or a combination thereof. In some embodiments, the reduced viscosity anti-myostatin formulation is a reconstituted formulation. Myostatin antibodies can be formulated as described herein as pharmaceutical compositions and used to treat disorders such as, but not limited to, muscular dystrophy, sarcopenia, cachexia, and Type II diabetes. In certain embodiments, a reduced viscosity anti-myostatin antibody formulation is provided as a kit. Such kits can include instructions for use of the antibody formulation.

In certain embodiments, the reduced viscosity protein formulation is a reduced viscosity anti-IL-12 antibody formulation. In one embodiment, the anti-IL-12 antibody is a monoclonal antibody. In another embodiment, the anti-IL-12 antibody is a humanized monoclonal antibody (e.g., a partially humanized or fully humanized monoclonal antibody). In certain embodiments, the anti-IL-12 antibody is J695. Anti-IL-12 antibodies are generally used in a formulation at a concentration of between about 25 mg/ml to about 400 mg/ml. A viscosity reducing agent is generally added to an anti-IL-12 antibody formulation to a final concentration of between about 1 mM and about 50 mM. In some embodiments, the viscosity reducing agent is added to an anti-IL-12 antibody formulation to a final concentration of between about 5 mM and about 25 mM. In certain embodiments, the viscosity reducing agent is added to an anti-IL-12 antibody formulation to a final concentration of between about 1 mM and about 15 mM. In certain other embodiments, the viscosity reducing agent is added to an anti-IL-12 antibody formulation to a final concentration of between 0.5 mM and about 14 mM. When the viscosity reducing agent is added to an anti-IL-12 antibody formulation to a concentration of between about 0.5 mM to about 50 mM, sodium chloride and sodium biphosphate are not used as viscosity reducing agents. Reduced viscosity anti-IL-12 antibody formulations generally have a pH of between about 5.5 and about 6.5. In certain embodiments, histidine is used as a buffer in a reduced viscosity IL-12 antibody formulation. Reduced viscosity anti-IL-12 antibody formulations can also include one or more cryoprotectants, one or more surfactants, one or more anti-oxidants, or combinations thereof. In some embodiments, the reduced viscosity anti-IL-12 antibody formulation is a reconstituted formulation. Anti-IL-12 antibodies can be formulated as described herein for use as pharmaceutical compositions and used to treat disorders such as, but not limited to, rheumatoid arthritis, Crohn's disease, psoriasis, and psoriatic arthritis. In certain embodiments, a reduced viscosity anti-IL-12 antibody formulation is provided as part of a kit. Such kits can include instructions for use of the anti-IL-12 antibody formulation.

In certain embodiments, the reduced viscosity protein formulation is an anti-IL-13 antibody formulation. In one embodiment, the anti-IL-13 antibody is a monoclonal antibody. In another embodiment, the anti-IL-13 antibody is a humanized monoclonal antibody (e.g., partially humanized or fully humanized). In certain embodiments, the anti-IL-13 antibody is IMA-638. Anti-IL-13 antibodies are generally used in a formulation at a concentration of between about 25 mg/ml to about 400 mg/ml. A viscosity reducing agent is generally added to make a reduced viscosity anti-IL-13 antibody formulation to a final concentration of between about 1 mM and about 50 mM. In some embodiments, the viscosity reducing agent is added to an anti-IL-13 antibody formulation to a final concentration of between about 5 mM and about 25 mM. In certain embodiments, the viscosity reducing agent is added to an anti-IL-13 antibody formulation to a final concentration of between about 1 mM and about 15 mM. In certain other embodiments, the viscosity reducing agent is added to an anti-IL-13 antibody formulation to a final concentration of between 0.5 mM and about 14 mM. When the viscosity reducing agent is added to an anti-IL-13 antibody formulation to a concentration of between about 0.5 mM to about 50 mM, sodium chloride and sodium biphosphate are not used as viscosity reducing agents. Reduced viscosity anti-IL-13 antibody formulations generally have a pH of between about 5.5 and about 6.5. In one embodiment, histidine is used as a buffer in a reduced viscosity IL-13 antibody formulation. A reduced viscosity anti-IL-13 antibody formulation can also include one or more cryoprotectants, one or more surfactants, one or more anti-oxidants, or combinations thereof. In some embodiments, the reduced viscosity anti-IL-13 formulation is a reconstituted formulation. Anti-IL-13 antibodies can be formulated in a reduced viscosity formulation as pharmaceutical composition and used to treat disorders such as, but not limited to, respiratory disorders (e.g., asthma); atopic disorders (e.g., allergic rhinitis); inflammatory and/or autoimmune conditions of the skin (e.g., atopic dermatitis), gastrointestinal organs (e.g., inflammatory bowel diseases (IBD)), as well as fibrotic and cancerous disorders. In certain embodiments, a reduced viscosity anti-IL-13 antibody formulation is provided as a kit. Such kits can include instructions for use of the reduced viscosity anti-IL-13 antibody formulation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE DRAWINGS

FIG. 3 is a graph depicting the results of experiments conducted to determine the effect of increasing concentrations of calcium chloride on the viscosity of an anti-IL-13 (IMA-638) antibody formulation.

FIG. 4A is a bar graph depicting the results of experiments conducted to test the effect of freeze-thaw-induced degradation of the anti-myostatin (MYO-029) antibody in the presence or absence of calcium chloride. Degradation was assessed by protein recovery as determined by measuring absorbance at 280 nm.

FIG. 4B is a bar graph depicting the results of experiments conducted to test the effect of freeze-thaw-induced degradation of the anti-myostatin (MYO-029) antibody in the presence or absence of calcium chloride. Degradation was assessed by percentage of high molecular weight species (% HMW) formation as determined by size exclusion-high performance liquid chromatography (SEC-HPLC).

FIG. 5A is a bar graph depicting the results of experiments conducted to test the effect of the presence or absence (control) of calcium chloride on the liquid stability of anti-myostatin (MYO-029) antibody subjected to storage at 40° C. for up to seven days. Liquid stability of MYO-029 antibody was determined by measuring absorbance at 280 nm.

FIG. 5B is a bar graph depicting the results of experiments conducted to test the effect of the presence or absence (control) of calcium chloride on the liquid stability of anti-myostatin (MYO-029) antibody subjected to storage at 40° C. for up to seven days. Liquid stability of MYO-029 antibody was determined by measuring HMW formation as determined by SEC-HPLC.

FIG. 6 is a representation of the amino acid sequence of the MYO-028 antibody heavy chain (SEQ ID NO:1) and light chain (SEQ ID NO:2).

FIG. 7 is a representation of the amino acid sequence of the MYO-029 antibody heavy chain (SEQ ID NO:3) and light chain (SEQ ID NO:4).

FIG. 8 is a representation of the amino acid sequence of the J695 antibody heavy chain (SEQ ID NO:5) and light chain (SEQ ID NO:6).

FIG. 9 is a representation of the amino acid sequence of the IMA-638 antibody heavy chain (SEQ ID NO:7) and light chain (SEQ ID NO:8). The last amino acid residue encoded by the heavy chain DNA sequence, $Lys^{448}$, is observed in the mature, secreted form of IMA-638 only in small quantities and is presumably removed from the bulk of the monoclonal antibody during intracellular processing by CHO cellular proteases. Therefore, the carboxy-terminus of the IMA-638 heavy chain is $Gly^{447}$. Carboxy-terminus lysine processing has been observed in recombinant and plasma-derived antibodies and does not appear to impact their function.

DETAILED DESCRIPTION

Figure 1:
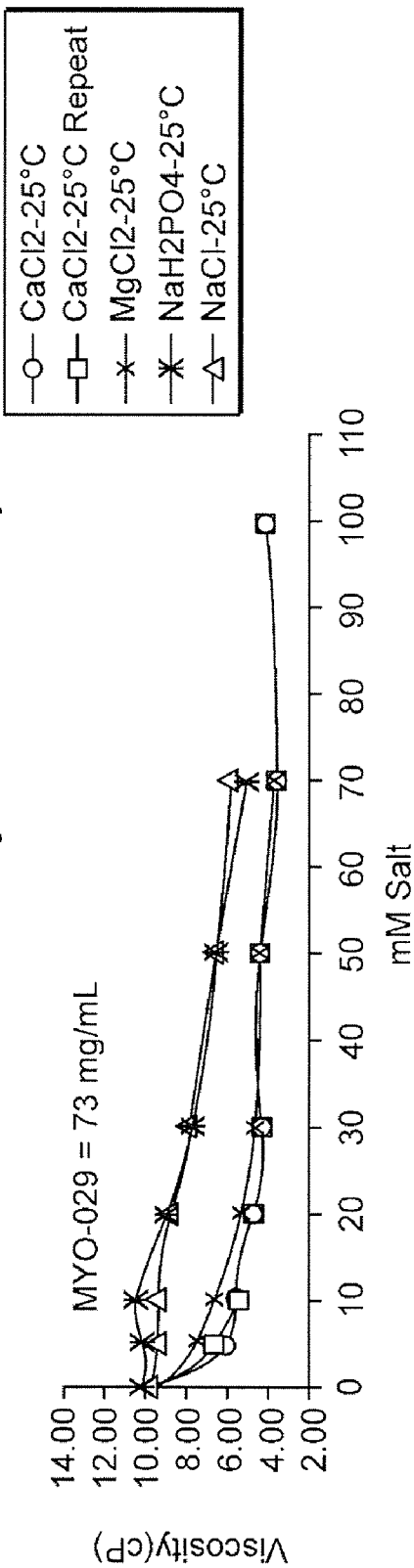
FIG. 1 is a graph depicting the results of experiments conducted to determine the effect of increasing concentrations of various salts on the viscosity of an anti-myostatin (MYO-029) antibody formulation.

The viscosity of a protein formulation has implications for the stability, processing, storage, and, for those used as drugs, drug delivery of the protein formulation to a patient. Such implications include, but are not limited to concentration and buffer exchange via ultrafiltration and diafiltration (the flux across the membrane may decrease with increasing viscosity thereby resulting in longer processing times), sterile filtration (it takes longer to sterile filter viscous solutions, and in some instances a very viscous solution will not pass through membranes with very small pores, e.g., 0.22 μm membranes), sample handling (e.g., difficulty with pipetting and the ability to draw into a syringe), recovery from the storage vial post reconstitution, stability, and passage through needles for subcutaneous or intramuscular administration.

Provided herein are methods of reducing the viscosity of a protein formulation that have been identified. The methods are suitable for preparing protein formulations having reduced viscosity ("reduced viscosity formulations" or "reduced viscosity protein formulations"). These reduced viscosity protein formulations include a protein of interest and a viscosity reducing agent.

Methods of Reducing the Viscosity of a Protein Formulation

The term "viscosity" as used herein, may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. If one fluid takes 100 seconds to complete its flow and another fluid takes 200 seconds, the second fluid is twice as viscous as the first on a kinematic viscosity scale. "Absolute viscosity," sometimes called "dynamic" or "simple viscosity," is the product of kinematic viscosity and fluid density. The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

The viscosity of a protein formulation can be reduced by the addition of a viscosity reducing agent to the formulation. In some cases, the viscosity reducing agent is added at a relatively low concentration. The viscosity of a formulation comprising a viscosity reducing agent is reduced compared to the viscosity of a formulation lacking the viscosity reducing agent. When the addition of the viscosity reducing agent results in lowering the viscosity of the formulation compared to a corresponding formulation that does not include the viscosity reducing agent or compared to a formulation that does not include the viscosity reducing agent at a selected concentration, the formulation containing the viscosity reducing agent (e.g., in a selected concentration), the formulation is a reduced viscosity formulation. In certain reduced viscosity formulations, the viscosity reducing agent generally reduces the viscosity of a protein formulation by about 5%, about 10%, about 15%, about 20%, about 25%, about 30%, about 35%, about 40%, about 45%, about 50%, about 55%, about 60%, about 65%, about 70%, about 75%, about 80%, about 85%, and about 90% compared to the viscosity of a protein formulation without, or containing lower amounts of, the viscosity reducing agent. In some cases, the viscosity reducing agent reduces the viscosity of a protein formulation by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, and at least 90% compared to the viscosity of a protein formulation without, or containing lower amounts of, the viscosity reducing agent. In certain embodiments, the viscosity of a protein formulation is measured prior to the addition of the viscosity reducing agent. In other embodiments, the viscosity of a protein formulation is measured after the addition of the viscosity reducing agent. Such measurements may be made hours (e.g., 1-23 hours), days (e.g., 1-10 days), weeks (e.g., 1-5 weeks), or months (e.g., 1-12 months), or years (e.g., 1-2 years, 1-3 years) after the addition of a viscosity reducing agent to a protein formulation. In yet other embodiments, the viscosity of the protein formulation is measured prior to and after the addition of the viscosity reducing agent. Methods of measuring viscosity are well known in the art and include, for example, using a capillary viscometer, or a cone-plate rheometer.

In one embodiment, the viscosity reducing agent is a salt such as calcium chloride, magnesium chloride, sodium phosphate, or arginine hydrochloride. In the method described herein, the viscosity reducing agent is added to the protein formulation to a final concentration of between about 0.5 mM and about 100 mM. In one embodiment, the viscosity reducing agent is added to the protein formulation to a final concentration of between about 5 mM and about 20 mM. In another embodiment, the viscosity reducing agent is added to the protein formulation to a final concentration of between 0.5 mM and 14 mM. In certain embodiments, the viscosity reducing agent is added to the protein formulation to a final concentration of between about 0.5 mM and not greater than 20 mM, or 19 mM, or 18 mM, or 17 mM, or 16 M, or 15 mM, or 14 mM, or 13 mM, or 12 mM, or 11 mM, or 10 mM. In general, when the viscosity reducing agent is added to the protein formulation to a final concentration of between about 0.5 mM and about 25 mM, the viscosity reducing agent is calcium chloride or magnesium chloride, but not sodium chloride, or sodium biphosphate. In certain embodiments, the viscosity reducing agent is added at low concentrations so as not to negatively impact the protein formulation. For example, at calcium chloride or magnesium chloride concentrations of 20 mM or greater, proteins may form a gel at low storage temperatures (e.g., 2-8° C.). Accordingly, a concentration of a viscosity reducing agent is generally selected for which the viscosity is reduced at the intended storage temperature of the reduced viscosity formulation.

Formulations

The composition of a reduced viscosity protein formulation is determined by consideration of several factors. These factors include, but are not limited to: the nature of the protein (e.g., receptor, antibody, Ig fusion proteins, enzyme); the concentration of the protein; the desired pH range; how the protein formulation is to be stored (e.g., temperature); the period of time over which the protein formulation is to be stored; and how the formulation is to be administered to a patient. The selection of an appropriate viscosity reducing agent is made based, in part, on such requirements for the protein in the formulation.

Proteins

The protein of interest to be formulated includes, but is not limited to, proteins such as, myostatin/GDF-8; interleukins (ILs), e.g., IL-1 to IL-15; growth hormones such as human growth hormone and bovine growth hormone; growth hormone releasing factor; parathyroid hormone; thyroid stimulating hormone; uricase; bikunin; bilirubin oxidase; subtilisin; lipoproteins; α-1-antitrypsin; insulin A-chain; insulin B-chain; proinsulin; follicle stimulating hormone; calcitonin; luteinizing hormone; glucagon; Factor VIIa; Factor VIII, Factor VIIIC; Factor IX; tissue factor; von Willebrand factor; anti-clotting factors such as Protein C; atrial natriuretic factor; lung surfactant; a plasminogen activator, such as urokinase or tissue-type plasminogen activator (t-PA); bombazine; thrombin; plasmin; miniplasmin; microplasmin; tumor necrosis factor-α and -β; enkephalinase; RANTES (Regulated on Activation Normally T-cell Expressed and Secreted); human macrophage inflammatory protein (MTP-1-α); serum albumin such as human serum albumin; Mullerian-inhibiting substance; relaxin A-chain; relaxin B-chain; prorelaxin; mouse gonadotropin-associated peptide; DNase; inhibin; activin; vascular endothelial growth factor (VEGF); placental growth factor (PlGF); receptors for hormones or growth factors; an integrin; protein A or protein D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β 1, TGF-β 2, TGF-β 3, TGF-β 4, or TGF-β 5; insulin-like growth factor-I and -II (IGF-I and IGF-II); des(1-3)-IGF-I (brain IGF-I); insulin-like growth factor binding proteins; CD proteins such as: CD2, CD3, CD4, CD8, CD9, CD19, CD20, CD22, CD28, CD34, and CD45; erythropoietin (EPO); thrombopoietin (TPO); osteoinductive factors; immunotoxins; a bone morphogenetic protein (BMP); an interferon such as interferon-α, -β, and -γ; a colony stimulating factor (CSF), e.g., M-CSF, GM-CSF, and G-CSF; superoxide dismutase; T-cell receptors; members of the HER receptor family such as the EGF receptor, HER2, HER3 or HER4 receptor; cell adhesion molecules such as LFA-1, VLA-4, ICAM-1, and VCAM; IgE; blood group antigens; flk2/flt3 receptor; obesity (OB) receptor; decay accelerating factor (DAF); a viral antigen such as, HIV gag, env, pol, tat, or rev proteins; homing receptors; addressins; immunoadhesins; and biologically active fragments, or variants of any of the above-listed polypeptides. In some formulations, more than one type of protein or fragment is included in the formulation.

The term "biologically active fragment" means a fragment of a protein that retains at least one of the functions of the protein from which it is derived. A biologically active fragment of an antibody includes an antigen-binding fragment of the antibody; a biologically active fragment of a receptor includes a fragment of the receptor that can still bind its ligand; a biologically active fragment of a ligand includes that portion of a ligand that can still bind its receptor; and a biologically active fragment of an enzyme includes that portion of the enzyme that can still catalyze a reaction catalyzed by the full length enzyme. In one embodiment, a biologically active fragment retains at least about 5% of the function of the protein from which it is derived. The function of a protein can be assayed by methods known in the art (e.g., testing antibody-antigen interactions, testing ligand-receptor interactions, testing enzymatic activity, testing transcriptional activity, or testing DNA-protein interactions). In some cases, the fragment is a therapeutically useful fragment, which may, for example, retain certain features of the protein from which it is derived (e.g., binding to a specific ligand) but does not cause cellular response elicited by the protein from which it is derived.

In certain embodiments, the protein to be formulated is an antibody. The antibody may be one that can bind to one of the above-mentioned proteins. The term "antibody" as used herein, includes polyclonal antibodies, monoclonal antibodies, antibody compositions with polyepitope specificities, bispecific antibodies, diabodies, or other purified preparations of antibodies and recombinant antibodies. The antibodies can be whole antibodies, e.g., of any isotype (IgG, IgA, IgE, IgM, etc.), or fragments thereof, which bind the antigen of interest. In a specific example of an antibody used in the present invention, the antibody to be formulated is an antibody having the IgG isotype. Antibodies can be fragmented using conventional or other techniques and the fragments screened for binding to an antigen of interest. Generally, an antibody fragment comprises the antigen-binding and/or the variable region of an intact antibody. Thus, the term antibody fragment includes segments of proteolytically cleaved or recombinantly prepared portions of an antibody molecule that are can selectively bind to a selected protein. Non-limiting examples of such proteolytic and/or recombinant fragments include Fab, F(ab')$_2$, Fab', Fv, and single chain antibodies (scFv) containing a V[L] and/or V[H] domain joined by a peptide linker. The scFvs may be covalently or noncovalently linked to form antibodies having two or more binding sites.

In some embodiments, the antibody is a humanized monoclonal antibody. The term "humanized monoclonal antibody" as used herein, is a monoclonal antibody from a non-human source (recipient) that has been altered to contain at least one or more of the amino acid residues found in the equivalent human monoclonal antibody (donor). A "fully humanized monoclonal antibody" is a monoclonal antibody from a non-human source that has been altered to contain all of the amino acid residues found in the antigen-binding region of the equivalent human monoclonal antibody. Humanized antibodies may also comprise residues that are not found either in the recipient antibody or the donor antibody. These modifications can be made to further refine and optimize antibody functionality. A humanized antibody may also optionally comprise at least a portion of a human immunoglobulin constant region (Fc).

In certain embodiments, an antibody used in a reduced viscosity formulation is an anti-myostatin antibody (e.g., MYO-022, MYO-028 (FIG. 6), MYO-029 (FIG. 7)). MYO-022, MYO-028, and MYO-029 antibodies are described in U.S. patent application Ser. No. 10/688,925 (Pub. No. 2004/0142382), which is incorporated herein by reference. In other embodiments, the antibody is an IL-12 antibody (e.g., J695 (FIG. 8)). The J695 antibody is described in U.S. Pat. No. 6,914,128, which is incorporated herein by reference. In yet another embodiment, the antibody is an anti-IL-13 antibody (e.g., IMA-638 (FIG. 9), CAT-354). Anti-IL-13 antibodies are described in U.S. patent application Ser. No. 11/149,309, which is incorporated herein by reference.

In some embodiments, the protein to be formulated is a fusion protein. In one embodiment, the fusion protein is an immunoglobulin (Ig) fusion protein. In a specific embodiment, the fusion protein comprises the IgG heavy chain constant region. In another embodiment, the fusion protein comprises an amino acid sequence corresponding to the hinge, CH2 and CH3 regions of human immunoglobulin Cγ1. Examples of Ig fusion proteins include CTLA4 Ig and VCAM2D-IgG. Methods of making fusion proteins are known in the art (e.g., U.S. Pat. Nos. 6,887,471 and 6,482,409).

In certain embodiments, the protein to be formulated is a protein that does not include a Factor VII polypeptide, or anti-IgE antibody.

A reduced viscosity formulation can contain more than one protein as necessary for the treatment of a particular disorder. The additional protein(s) typically have complementary activities to the other protein(s) in the formulation, and do not adversely affect the other protein(s) in the formulation. For example, it may be desirable to provide a single formulation containing two or more antibodies that bind to myostatin; two or more antibodies that bind to IL-12; or two or more antibodies that bind to IL-13. In addition, a protein formulation can also contain non-protein substances that are of use in the ultimate utility of the reduced viscosity protein formulation. For example, sucrose can be added to enhance stability and solubility of the protein in solution; and histidine can be added to provide appropriate buffer capacity. Such additional substances can be part of a protein formulation prior to addition of a viscosity reducing agent or added in the process for making a reduced viscosity formulation.

In certain embodiments, the protein to be formulated is essentially pure and/or essentially homogeneous (i.e., substantially free from contaminating proteins, etc.) prior to its use in the formulation. The term "essentially pure" protein means a composition comprising at least about 90% by weight of a selected protein fraction, for example at least about 95% by weight of the selected protein fraction. The term "essentially homogeneous" protein means a composition comprising at least about 99% by weight of a selected protein fraction, excluding the mass of various stabilizers and water in solution.

Concentration of the Protein in a Low Viscosity Formulation

The concentration of the protein in a reduced viscosity formulation is dependent on the ultimate use of the formulation. Protein concentrations in the formulations described herein are generally between about 10 mg/ml and about 300 mg/ml, e.g., between about 10 mg/ml and about 100 mg/ml, about 25 mg/ml and about 100 mg/ml, about 50 mg/ml and about 100 mg/ml, about 75 mg/ml and about 100 mg/ml, about 100 mg/ml and about 200 mg/ml, about 125 mg/ml and about 200 mg/ml, about 150 mg/ml and about 200 mg/ml, about 200 mg/ml and about 300 mg/ml, and about 250 mg/ml and about 300 mg/ml. For example, protein concentrations in the formulations described herein can be between 10 mg/ml and 300 mg/ml, e.g., between 10 mg/ml and 100 mg/ml, between 25 mg/ml and 100 mg/ml, between 50 mg/ml and 100 mg/ml, between 75 mg/ml and 100 mg/ml, between 100 mg/ml and 200 mg/ml, between 125 mg/ml and 200 mg/ml, between 150 mg/ml and 200 mg/ml, between 200 mg/ml and 300 mg/ml, and between 250 mg/ml and 300 mg/ml. The term "between" is intended to be inclusive of the minimal and maximal concentrations.

Reduced viscosity protein formulations can be used for therapeutic purposes. Accordingly, the concentration of the protein in a formulation used for a therapeutic application is determined based on providing the protein in a dosage and volume that is tolerated by, and of therapeutic value to, the patient. If a reduced viscosity formulation is to be administered by injection, the protein concentration will be dependent on the injection volume (usually 1.0 mL-1.2 mL). Protein based therapies can require several mg/kg of dosing per week, per month, or per several months. Accordingly, if a protein is to be provided at 2-3 mg/kg of body weight of the patient, and an average patient weighs 75 kg, 150 mg-225 mg of the protein will need to be delivered in a 1.0 mL-1.2 mL injection volume. Alternatively, the formulation is provided in a concentration suitable for delivery at more than one injection site per treatment.

As the concentration of the protein in a formulation increases, the viscosity of the protein formulation is also likely to increase. Increased viscosity of the formulation makes the formulation harder to administer. Accordingly, there is a need to decrease the viscosity of protein formulations when the increased viscosity impacts its ability to be utilized.

Viscosity Reducing Agents

It has been found that adding relatively low concentrations of certain viscosity reducing agents to a protein formulation reduces the viscosity of the protein formulation. The term "viscosity reducing agent" as used herein, includes any agent that reduces the viscosity of a protein formulation compared to a protein formulation not containing, or containing a lesser amount of, the viscosity reducing agent. For example, a viscosity reducing agent generally reduces the viscosity of a protein formulation by about 5%, about 10%, about 20%, about 30%, about 40%, about 50%, about 60%, about 70%, about 90%, or about 95% compared to the viscosity of the protein formulation without, or containing lower amounts of, a viscosity reducing agent. For example, a viscosity reducing agent generally reduces the viscosity of the protein formulation by 5%, 10%, 20%, 30%, 40%, 50%, 60%, 70%, 90%, or 95% compared to the viscosity of a protein formulation without, or containing lower amounts of, the viscosity reducing agent. Non-limiting examples of viscosity reducing agents include calcium chloride, magnesium chloride, arginine hydrochloride, sodium chloride, sodium thiocyanate, ammonium thiocyanate, ammonium sulphate, sodium phosphate, and ammonium chloride.

In one embodiment, the viscosity reducing agent is calcium chloride. In another embodiment, the viscosity reducing agent is magnesium chloride. In an alternate embodiment, more than one viscosity reducing agent is added to a protein formulation.

A viscosity reducing agent is generally added to a protein formulation to a final concentration of between 1 mM to about 150 mM, e.g., between about 1 mM and about 50 mM, between about 2 mM and about 40 m, between about 3 mM and about 30 mM, between about 4 mM and about 25 mM, between about 5 mM and about 20 mM, between about 5 mM and about 25 mM, between about 5 mM and about 30 mM, between about 5 mM and about 40 mM, and between about 5 mM and about 50 mM. In certain embodiments, the viscosity reducing agent is added to the protein formulation to a final concentration of less than 14 mM, less than 13 mM, less than 12 mM, less than 11 mM, less than 10 mM, less than 9 mM, less than 8 mM, less than 7 mM, less than 6 mM, less than 5 mM, less than 4 mM, less than 3 mM, or less than 2 mM. In other embodiments, the viscosity reducing agent is added to the protein formulation to a final concentration of between 0.5 mM and 14 mM, between 0.5 mM and 13 mM, between 0.5 mM and 12 mM, between 0.5 mM and 11 mM, between 0.5 mM and 10 mM, between 0.5 mM and 9 mM, between 0.5 mM and 8 mM, between 0.5 mM and 7 mM, between 0.5 mM and 6 mM, or between 0.5 mM and 5 mM. In one embodiment, the viscosity reducing agent is calcium chloride at a final concentration of between about 5 mM and about 20 mM in the formulation. In another embodiment, the viscosity reducing agent is calcium chloride at a final concentration of between 5 mM and about 14 mM in the formulation. In other embodiments, the viscosity reducing agent is magnesium chloride at a final concentration of between about 5 mM and about 20 mM in the formulation. In another embodiment, the viscosity reducing agent is magnesium chloride at a final concentration of between 5 mM and about 14 mM in the formulation.

The viscosity of a protein formulation can be measured by any suitable method known in the art including, for example, using a capillary viscometer or a cone-plate rheometer.

Buffers

The term "buffer" as used herein, includes those agents that maintain the pH of a solution, e.g., a formulation, in a desired range. The pH of a formulation as described herein is generally between about pH 5.0 to about 9.0, for example, about pH 5.5 to about 6.5, about pH 5.5 to about 6.0, about pH 6.0 to about 6.5, pH 5.5, pH 6.0, or pH 6.5. In general, a buffer that can maintain a solution at pH 5.5 to 6.5 is used. Non-limiting examples of buffers that can be used in a formulation described herein include, histidine, succinate, gluconate, tris (trometamol), phosphate, citrate, 2-morpholinoethanesulfonic acid (MES), sodium phosphate, sodium acetate, and cacodylate.

Histidine is a buffer that is typically in reduced viscosity formulations that are to be administered by subcutaneous, intramuscular, or peritoneal injection. The concentration of the buffer is between about 5 mM and 30 mM. In one embodiment, the buffer of a formulation is histidine at a concentration of about 5 mM to about 20 mM.

Excipients

In addition to the protein, a viscosity reducing agent, and buffer, a reduced viscosity formulation as described herein may also contain other substances. Such substances include, but are not limited to, cryoprotectants, lyoprotectants, surfactants, bulking agents, anti-oxidants, and stabilizing agents. In one embodiment, a reduced viscosity protein formulation described herein includes an excipient selected from the group consisting of a cryoprotectant, a lyoprotectant, a surfactant, a bulking agent, an anti-oxidant, a stabilizing agent, and combinations thereof.

The term "cryoprotectant" as used herein, includes agents that provide stability to the protein in a formulation against freezing-induced stresses, e.g., by being preferentially excluded from the protein surface. Cryoprotectants may also offer protection during primary and secondary drying and long-term product storage. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g., PS-20 or PS-80); and amino acids, such as glycine, arginine, leucine, and serine. A cryoprotectant exhibiting low toxicity in biological systems is generally used. The cryoprotectant, if included in the formulation, is generally added to a final concentration of between about 0.1% and about 10% (weight/volume), e.g., between about 0.5% and about 10%, between about 0.5% and about 5%, between about 0.5% and about 2%, between about 1% and about 5%, or between about 5% and about 10%. In one embodiment, the cryoprotectant is sucrose at a concentration of between about 0.5% and about 10% (weight/volume).

In one embodiment, a lyoprotectant is added to a formulation described herein. The term "lyoprotectant" as used herein, includes agents that provide stability to the protein during the freeze-drying or dehydration process (primary and secondary freeze-drying cycles), e.g., by providing an amorphous glassy matrix and by binding with the protein through hydrogen bonding, replacing the water molecules that are removed during the drying process. This helps to maintain the protein conformation, minimize protein degradation during the lyophilization cycle, and improve the long-term product stability. Non-limiting examples of lyoprotectants include sugars, such as sucrose or trehalose; an amino acid, such as monosodium glutamate, non-crystalline glycine or histidine; a methylamine such, as betaine; a lyotropic salt, such as magnesium sulfate; a polyol, such as trihydric or higher sugar alcohols, e.g., glycerin, erythritol, glycerol, arabitol, xylitol, sorbitol, and mannitol; propylene glycol; polyethylene glycol; pluronics; and combinations thereof. The amount of lyoprotectant added to a formulation is generally an amount that does not lead to an unacceptable amount of degradation/aggregation of the protein when the protein formulation is lyophilized. Where the lyoprotectant is a sugar (such as sucrose or trehalose) and the protein is an antibody, non-limiting examples of lyoprotectant concentrations in a reduced viscosity protein formulation are from about 10 mM to about 400 mM, from about 30 mM to about 300 mM, and from about 50 mM to about 100 mM.

In certain embodiments, a surfactant is included in a formulation described herein. The term "surfactant" as used herein, includes agents that reduce the surface tension of a liquid by adsorption at the air-liquid interface. Examples of surfactants include, without limitation, nonionic surfactants, such as polysorbates (e.g., polysorbate 80 or polysorbate 20); poloxamers (e.g., poloxamer 188); Triton™ (e.g., Triton™X-100); sodium dodecyl sulfate (SDS); sodium octyl glycoside; lauryl-sulfobetaine; myristyl-sulfobetaine; linoleyl-sulfobetaine; stearyl-sulfobetaine; lauryl-sarcosine; myristyl-sarcosine; linoleyl-sarcosine; stearyl-sarcosine; linoleyl-betaine; myristyl-betaine; cetyl-betaine; lauroamidopropyl-betaine; cocamidopropyl-betaine; linoleamidopropyl-betaine; myristamidopropyl-betaine, palmidopropyl-betaine; isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the Monaquat-™ series (Mona Industries, Inc., Paterson, N.J.); polyethyl glycol; polypropyl glycol; and copolymers of ethylene and propylene glycol (e.g., pluronics, PF68). The amount of surfactant added is such that it maintains aggregation of the reconstituted protein at an acceptable level as assayed using, e.g., SEC-HPLC to determine the percentage of high molecular weight (HMW) species or low molecular weight (LMW) species, and minimizes the formation of particulates after reconstitution of a lyophilate of a protein formulation described herein. For example, the surfactant can be present in a formulation (liquid or prior to lyophilization) in an amount from about 0.001-0.5%, e.g., from about 0.05-0.3%.

In some embodiments, a bulking agent is included in a reduced viscosity formulation. The term "bulking agent" as used herein, includes agents that provide the structure of the freeze-dried product without interacting directly with the pharmaceutical product. In addition to providing a pharmaceutically elegant cake, bulking agents may also impart useful qualities in regard to modifying the collapse temperature, providing freeze-thaw protection, and enhancing the protein stability over long-term storage. Non-limiting examples of bulking agents include mannitol, glycine, lactose, and sucrose. Bulking agents may be crystalline (such as glycine, mannitol, or sodium chloride) or amorphous (such as dextran or hydroxyethyl starch) and are generally used in protein formulations in an amount from 0.5% to 10%.

Other pharmaceutically acceptable carriers, excipients, or stabilizers, such as those described in Remington: The Science and Practice of Pharmacy 20th edition, Gennaro, Ed., Lippincott Williams & Wilkins (2000) may also be included in a protein formulation described herein, provided that they do not adversely affect the desired characteristics of the formulation. Acceptable carriers, excipients, or stabilizers are nontoxic to recipients (e.g., patients) at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinsitol, galactose, galactitol, glycerol, cyclitols (e.g., inositol), polyethylene glycol; sulfur containing reducing agents, such as urea, glutathione, thioctic acid, sodium thioglycolate, thioglycerol, α-mono-thioglycerol, and sodium thio sulfate; low molecular weight proteins, such as human serum albumin, bovine serum albumin, gelatin, or other immunoglobulins; and hydrophilic polymers, such as polyvinylpyrrolidone.

Exemplary Protein Formulations

MY-029

In one example, a MYO-029 reduced viscosity formulation can be formulated using 1 mg/ml to 300 mg/ml of the MYO-029 antibody. The MYO-029 formulation generally includes between about 1 mM and about 50 mM calcium chloride or magnesium chloride. The formulation can include about 5 mM to about 25 mM histidine. The formulation can include about 1% to about 5% (w/v) sucrose or trehalose. In some instances, the formulation can include about 10 mM to about 25 mM methionine. In certain MYO-029 formulations, 0.05-0.2% (w/v) polysorbate-20 or polysorbate-80 is added. The pH of the formulation is generally between 5.5 and 6.5. In a specific example, the MYO-029 formulation comprises 150 mg/ml of the MYO-029 antibody, 10 mM calcium chloride or magnesium chloride, 20 mM histidine, 4% sucrose, and has a pH of 6.0. In another specific example, the MYO-029 formulation comprises 75 mg/ml of the MYO-029 antibody, 5 mM calcium chloride or magnesium chloride, 10 mM histidine, 10 mM methionine, 2% sucrose, and has a pH of 6.0. In another specific example, a MYO-029 antibody formulation comprises 150 mg/ml of the MYO-029 antibody, 10 mM calcium chloride or magnesium chloride, 20 mM histidine, 20 mM methionine, 4% sucrose, 0.2% polysorbate-80, and has a pH of 6.0.

MYO-028

MYO-028 reduced viscosity formulations can be formulated using 1 mg/ml to 300 mg/ml of the MYO-028 antibody. The MYO-028 formulation generally includes between about 1 mM and about 50 mM calcium chloride or magnesium chloride. The formulation can include between about 5 mM to about 25 mM histidine. The formulation can include between about 1% to about 5% (w/v) sucrose or trehalose. The pH of a MYO-028 formulation is generally between about 5.5 and about 6.5. In one specific example, a MYO-028 antibody formulation comprises 50 hs mg/ml of the antibody, 10 mM histidine, 5% sucrose, and has a pH of 6.5. In another specific example, a MYO-028 antibody formulation comprises 50 mg/ml of the antibody, 10 mM calcium chloride or magnesium chloride, 10 mM histidine, 5% sucrose, and has a pH of 6.5.

J695

J695 reduced viscosity formulations can be formulated using 1 mg/ml to 300 mg/ml of the J695 antibody. A J695 formulation generally includes between about 1 mM and about 50 mM calcium chloride or magnesium chloride. The formulation can include about 5 mM to about 25 mM histidine. The formulation may include about 1% to about 5% (w/v) sucrose or trehalose. In some instances, the formulation can include about 10 mM to about 25 mM methionine. In certain J695 formulations, between about 1% to about 5% (w/v) mannitol is added. The pH of the formulation is generally between 5.5 and 6.5. In a specific example, a J695 antibody formulation comprises 100 mg/ml of the J695 antibody, 10 mM histidine, 10 mM methionine, 4% mannitol, 1% sucrose, and has a pH of 6.0. In another specific example, a J695 antibody formulation comprises 100 mg/ml of the J695 antibody, 10 mM histidine, 10 mM methionine, 5 mM calcium chloride or magnesium chloride, 4% mannitol, 1% sucrose, and has a pH of 6.0. In another specific embodiment, the J695 antibody formulation comprises 100 mg/ml of the J695 antibody, 10 mM histidine, 10 mM methionine, 10 mm calcium chloride or magnesium chloride, 4% mannitol, 1% sucrose, and has a pH of 6.0.

IMA-638

IMA-638 protein formulations can be formulated using 1 mg/ml to 300 mg/ml of the IMA-638 antibody. A reduced viscosity formulation containing IMA-638 generally includes between about 1 mM and about 50 mM calcium chloride or magnesium chloride. The formulation can include about 5 mM to about 25 mM histidine. The formulation can also include about 1% to about 10% (w/v) sucrose or trehalose. The pH of the formulation is generally between 5.5 and 6.5. In a specific example, the IMA-638 antibody formulation comprises 50 mg/ml of the IMA-638 antibody, 10 mM histidine, 5% sucrose, and has a pH of 6.0. In another specific example, the IMA-638 antibody formulation comprises 100 mg/ml of the IMA-638 antibody, 20 mM histidine, 10% sucrose, and has a pH of 6.0. In another specific example, the IMA-638 antibody formulation comprises 50 mg/ml of the IMA-638 antibody, 5 mM calcium chloride or magnesium chloride, 10 mM histidine, 10% sucrose, and has a pH of 6.0. In yet another specific example, the IMA-638 antibody formulation comprises 100 mg/ml of the IMA-638 antibody, 10 mM calcium chloride or magnesium chloride, 20 mM histidine, 10% sucrose, and has a pH of 6.0.

Storage Methods

A reduced viscosity protein formulation described herein may be stored by any suitable method known to one of skill in the art. Non-limiting examples of methods for preparing a reduced viscosity formulation for storage include freezing, lyophilizing, and spray drying the protein formulation.

In some cases, a reduced viscosity formulation is frozen for storage. Accordingly, it is desirable that the formulation be relatively stable under such conditions, including when subjected to freeze-thaw cycles. One method of determining the suitability of a formulation for frozen storage is to subject a sample formulation to at least two, e.g. three to ten cycles of freezing (at, for example −20° C. or −80° C.) and thawing (for example by fast thaw at room temperature or slow thaw on ice), determining the amount of LMW species and/or HMW species that accumulate after the freeze-thaw cycles and comparing it to the amount of LMW species or HMW species present in the sample prior to the freeze-thaw procedure. An increase in the LMW species or HMW species indicates decreased stability of a protein stored as part of the formulation. Size exclusion high performance liquid chromatography (SEC-HPLC) can be used to determine the presence of LMW and HMW species. A suitable formulation may accumulate undesirable HMW species or LMW species, but not to the extent that the presence of the HMW species or LMW species make the formulation unsuitable for its intended use.

In some cases, a formulation is stored as a liquid. Accordingly, it is desirable that the liquid formulation be relatively stable under such conditions, including at various temperatures. One method of determining the suitability of a formulation for liquid storage is to store the sample formulation at several temperatures (such as 2-8° C., 15° C., 20° C., 25° C., 30° C., 35° C., 40° C., and 50° C.) and monitoring the amount (e.g., change in percentage) of HMW species and/or LMW species that accumulate over time. Additionally, the charge profile of the protein may be monitored by cation exchange-high performance liquid chromatography (CEX-HPLC).

In general, the percentage of high molecular weight species or low molecular weight species is determined either as a percentage of the total protein content in a formulation or as a change in the percentage increase over time (i.e., during storage), as is appropriate for the assay and parameter being determined. In general, and in non-limiting examples, the change in the percentage of protein in high molecular weight species or low molecular weight species in a reduced viscosity formulation is not greater than 10%, e.g., not greater than about 8%, not greater than about 5%, or not greater than about 3% with respect to the assayed parameter (e.g., time, temperature, additional compounds in the formulation, lyophilization, or shaking).

Alternatively, a formulation can be stored after lyophilization. The term "lyophilization" as used herein, refers to a process by which the material to be dried is first frozen followed by removal of the ice or frozen solvent by sublimation in a vacuum environment. An excipient (e.g., lyoprotectant) may be included in formulations that are to be lyophilized so as to enhance stability of the lyophilized product upon storage. The term "reconstituted formulation" as used herein, refers to a formulation that has been prepared by dissolving a lyophilized protein formulation in a diluent such that the protein is dispersed in the diluent. The term "diluent" as used herein, is a substance that is pharmaceutically acceptable (safe and non-toxic for administration to a human) and is useful for the preparation of a liquid formulation, such as a formulation reconstituted after lyophilization. Non-limiting examples of diluents include sterile water, bacteriostatic water for injection (BWFI), a pH buffered solution (e.g., phosphate-buffered saline), sterile saline solution, Ringer's solution, dextrose solution, or aqueous solutions of salts and/or buffers.

Testing a reduced viscosity formulation for the stability of the protein component of the formulation after lyophilization is useful for determining the suitability of a formulation. The method is similar to that described above for freezing, except that the sample formulation is lyophilized instead of frozen, reconstituted using a diluent and the reconstituted formulation is tested for the presence of LMW species and/or HMW species. An increase in LMW species or HMW species in the lyophilized sample compared to a corresponding sample formulation that was not lyophilized indicates decreased stability in the lyophilized sample.

In some cases, a formulation is spray-dried and then stored. For spray drying, a liquid formulation is aerosolized in the presence of a dry gas stream. Water is removed from the formulation droplets into the gas stream, resulting in dried particles of the drug formulation. Excipients may be included in the formulation to (1) protect the protein during the spray-drying dehydration, (2) protect the protein during storage after spray drying, and/or (3) give the solution properties suitable for aerosolization. The method is similar to that described above for freezing, except that the sample formulation is spray-dried instead of frozen, reconstituted in a diluent and the reconstituted formulation is tested for the presence of LMW species and/or HMW species. An increase in LMW or HMW species in the spray-dried sample compared to a corresponding sample formulation that was not lyophilized indicates decreased stability in the spray-dried sample.

Methods of Treatment

The reduced viscosity formulations described herein are useful as pharmaceutical compositions in the treatment and/or prevention of a disease or disorder in a patient in need thereof. The term "treatment" refers to both therapeutic treatment and prophylactic or preventative treatment. Treatment includes the application or administration of the reduced viscosity formulation to the body, an isolated tissue, or cell from a patient who has a disorder, a symptom of a disorder, is at risk for a disorder, or a predisposition toward a disorder, with the purpose to cure, heal, alleviate, relieve, alter, remedy, ameliorate, improve, or affect the disorder, the symptom of the disorder, or the predisposition toward the disorder. Those "in need of treatment" include those who already have a disorder, as well as those in whom a disorder is to be prevented. The term "disorder" is any condition that would benefit from treatment with a protein formulation described herein. This includes chronic and acute disorders or diseases including those pathological conditions that predispose the subject (patient) to the disorder in question. Non-limiting examples of disorders to be treated using a formulation described herein include autoimmune disorders, inflammatory disorders, muscle wasting disorders, allergies, cancers, muscular dystrophy, sarcopenia, cachexia, Type II diabetes, rheumatoid arthritis, Crohn's disease, psoriasis, psoriatic arthritis, asthma, dermatitis, allergic rhinitis, chronic obstructive pulmonary disease, eosinophilia, fibrosis, and excess mucus production.

In one embodiment, the reduced viscosity formulation suitable for use as a pharmaceutical composition comprises an anti-myostatin antibody and a viscosity reducing agent. In one embodiment, the anti-myostatin antibody is MYO-029. In other embodiments, the anti-myostatin antibody is MYO-022 or MYO-028. The anti-myostatin antibody is generally at a concentration of between about 0.5 mg/ml and about 300 mg/ml in the formulation. In another embodiment, the viscosity reducing agent is at a final concentration of between about 0.5 mM and 20 mM in the pharmaceutical composition. In another embodiment, the viscosity reducing agent is at a final concentration of between about 0.5 mM and 14 mM in the pharmaceutical composition. In another embodiment, the pharmaceutical composition comprises an anti-myostatin antibody, a viscosity reducing agent, and a buffer wherein the pH of the formulation is between about 5.5 to about 6.5. The pharmaceutical compositions described herein may also contain other proteins, drugs, and/or excipients. In particular, other proteins or substances useful for treating the disorder in question may be added to the formulation. Anti-myostatin antibody-containing pharmaceutical compositions are useful in the treatment or prevention of disorders such as, but not limited to, muscle wasting disorders, muscular dystrophy, sarcopenia, cachexia, and Type II diabetes.

In another embodiment, a pharmaceutical composition comprises an anti-IL-12 antibody and a viscosity reducing agent. In one embodiment, the anti-IL-12 antibody is J695. The anti-IL-12 antibody is generally at a concentration of between about 0.5 mg/ml and about 300 mg/ml in the formulation. In another embodiment, the viscosity reducing agent is at a final concentration of between about 0.5 mM and 20 mM in the pharmaceutical composition. In another embodiment, the viscosity reducing agent is at a final concentration of between about 0.5 mM and 14 mM in the pharmaceutical composition. In another embodiment, the pharmaceutical composition comprises an anti-IL-12 antibody, a viscosity reducing agent, and a buffer, wherein the pH of the formulation is between about 5.5 to about 6.5. The pharmaceutical compositions described herein may also contain other proteins, drugs, and/or excipients. In particular, other proteins or substances useful for treating the disorder in question may be added to the formulation. Anti-IL-12 antibody containing pharmaceutical compositions are useful in the treatment or prevention of disorders such as, but not limited to, autoimmune disorders, inflammatory disorders, rheumatoid arthritis, Crohn's disease, psoriasis, and psoriatic arthritis.

In another embodiment, a pharmaceutical composition comprises an anti-L-13 antibody and a viscosity reducing agent. In one embodiment, the anti-IL-13 antibody is IMA-638. The anti-IL-13 antibody is generally at a concentration of between about 0.5 mg/ml and about 300 mg/ml in the formulation. In another embodiment, the viscosity reducing agent is at a final concentration of between about 0.5 mM and 20 mM in the pharmaceutical composition. In another embodiment, the viscosity reducing agent is at a final concentration of between about 0.5 mM and 14 mM in the pharmaceutical composition. In another embodiment, the pharmaceutical composition comprises an anti-IL-13 antibody, a viscosity reducing agent, and a buffer wherein the pH of the formulation is between about 5.5 to about 6.5. The pharmaceutical compositions described herein may also contain other proteins, drugs, and/or excipients. In particular, other proteins or substances useful for treating the disorder in question may be added to the formulation. Anti-IL-13 antibody containing pharmaceutical compositions are useful in the treatment or prevention of disorders such as, but not limited to, asthmatic disorders, atopic disorders, chronic obstructive pulmonary disease, conditions involving airway inflammation, eosinophilia, fibrosis and excess mucus production, inflammatory conditions, autoimmune conditions, tumors or cancers, and viral infection.

Administration

A reduced viscosity formulation described herein can be administered to a subject in need of treatment using methods known in the art, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation, or by sustained release or extended-release means. If the formulation has been lyophilized, the lyophilized material is first reconstituted in an appropriate liquid prior to administration. The lyophilized material can be reconstituted in, e.g., BWFI, phosphate buffered saline, or the same formulation the protein had been in prior to lyophilization.

Parenteral compositions can be prepared in dosage unit form for ease of administration and uniformity of dosage. "Dosage unit form" as used herein, refers to physically discrete units suited as unitary dosages for the subject to be treated; each unit containing a predetermined quantity of active compound calculated to produce the desired therapeutic effect in association with the selected pharmaceutical carrier.

In the case of an inhalation method, such as metered dose inhaler, the device is designed to deliver an appropriate amount of a formulation. For administration by inhalation, the compounds are delivered in the form of an aerosol spray from a pressured container or dispenser that contains a suitable propellant, e.g., a gas, such as carbon dioxide, or a nebulizer. Alternatively, an inhaled dosage form may be provided as a dry powder using a dry powder inhaler.

A reduced viscosity formulation can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles, and nanocapsules) or in macroemulsions. Such techniques are disclosed in *Remington's Pharmaceutical Sciences,* 20th edition (supra).

Sustained-release preparations of the protein formulations described herein can also be prepared. Suitable examples of sustained-release preparations include semipermeable matrices of solid hydrophobic polymers containing the protein formulation. Examples of sustained-release matrices include polyesters, hydrogels (for example, poly(2-hydroxyethyl-methacrylate), or poly(vinylalcohol)), polylactides, copolymers of L-glutamic acid and γ-ethyl-L-glutamate, non-degradable ethylene-vinyl acetate, degradable lactic acid-glycolic acid copolymers, and poly-D-(-)-3-hydroxybutyric acid. The sustained-release formulations of the proteins described herein can be developed using e.g., polylactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Liposomal compositions can also be used to formulate the proteins or antibodies disclosed herein.

Dosing

Toxicity and therapeutic efficacy of a formulation can be determined by pharmaceutical procedures known in the art using, for example, cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$.

The data obtained from the cell culture assays and animal studies can be used in formulating a range of dosage for use in humans. The dosage of such formulations generally lies within a range of circulating concentrations that include the $ED_{50}$ with little or no toxicity. The dosage may vary within this range depending upon the dosage form employed and the route of administration utilized. For any formulation used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The appropriate dosage of the protein of the formulation will depend on the type of disorder to be treated, the severity and course of the disorder, whether the agent is administered for preventive or therapeutic purposes, previous therapy, the patient's clinical history and response to the agent, and the discretion of the attending physician. A formulation is generally delivered such that the dosage is between about 0.1 mg protein/kg of body weight to 100 mg protein/kg of body weight. The formulation is administered to the patient at one time or over a series of treatments, In one embodiment, a myostatin antibody (e.g., MYO-22, MYO-28, MYO-029) formulation is delivered to a patient in need thereof at a dosage of 1 mg/kg to 10 mg/kg of body weight. In another embodiment, an IL-12 antibody formulation is administered to a patient in need thereof at a dosage of 1 mg/kg to 5 mg/kg of body weight. In a further embodiment, an IL-13 antibody formulation is administered to a patient in need thereof at a dosage of about 0.5 mg/kg to about 5 mg/kg of body weight of the patient.

A formulation to be used for in vivo administration must be sterile. A formulation can be rendered sterile for example, by filtration through sterile filtration membranes, prior to, or following, formulation of a liquid or lyophilization and reconstitution. The therapeutic compositions disclosed herein generally are placed into a container having a sterile access port, for example, an intravenous solution bag, or vial having a stopper pierceable by a hypodermic injection needle.

Articles of Manufacture

In another embodiment, an article of manufacture is provided that contains a formulation described herein and typically provides instructions for its use. The article of manufacture comprises a container suitable for containing the formulation. Suitable containers include, without limitation, bottles, vials (e.g., dual chamber vials), syringes (e.g., single or dual chamber syringes), test tubes, nebulizers, inhalers (e.g., metered dose inhalers or dry powder inhalers), or depots. The container can be formed from a variety of materials, such as glass, metal or plastic (e.g., polycarbonate, polystyrene, polypropylene). The container holds the formulation and the label on, or associated with, the container can indicate directions for reconstitution and/or use. The label may further indicate that the formulation is useful or intended for subcutaneous administration. The container holding the formulation may be a multi-use vial, which allows for repeat administrations (e.g., from 2-6 doses) of the formulation. The article of manufacture may further comprise a second container comprising a suitable diluent (e.g., WFI, 0.9% NaCl, BWFI, or phosphate buffered saline). When the article of manufacture comprises a lyophilized version of a protein formulation, mixing of a diluent with the lyophilized formulation will provide a final protein concentration in the reconstituted formulation of generally at least 20 mg/ml. The article of manufacture may further include other materials desirable from a commercial and user standpoint, including other buffers, diluents, filters, needles, syringes, and package inserts with instructions for use.

The invention is further illustrated by the following examples. The examples are provided for illustrative purposes only. They are not to be construed as limiting the scope or content of the invention in any way.

EXAMPLES

Example 1

Viscosity of Antibody Formulations

Anti-β-amyloid peptide (anti-AB), anti-IL-13, anti-IL-12 (J695) and anti-myostatin (MYO-029) antibodies were formulated as described in Table 1. The viscosity of these antibody formulations was measured using an Anton Paar Physica MCR301 cone and plate rheometer. Specifically, a CP25-1 (24.971 mm diameter, 1.002° angle) cone was used for all of the measurements; the shear rate was constant at 898 1/s for a duration of 100 seconds. Measurements were made every 10 seconds. The viscosity measurements were performed at both 4° C. and 25° C. using a built-in Peltier temperature control unit. The liquid sample load on the plate was 90 μl. Each sample was analyzed in triplicate.

Table 1 below lists the viscosities of different antibodies at different concentrations and in different formulations.

TABLE 1

| Antibody | Formulation | Conc. (mg/ml) | Viscosity at 25° C. (cP) | Viscosity at 4° C. (cP) |
|---|---|---|---|---|
| Anti-AB | 10 mM Histidine, 10 mM Methionine. pH 6.0 | 160 | 5.18 | 9.77 |
| Anti-IL-13 | 20 mM Histidine, 10% Sucrose, pH 6.0 | 100 | 7.18 | 16.44 |
| J695 | 10 mM Histidine, 10 mM Methionine, 4% Mannitol, 1% Sucrose, pH 6.0 | 100 | 6.81 | 18.43 |
| MYO-029 | 20 mM Histidine, 4% Sucrose, pH 6.0 | 70 | 2 | 5 |
| MYO-029 | 10 mM Histidine, 10 mM Methionine, 2% Sucrose, pH 6.0 | 114 | 14.71 | 61.74 |
| MYO-029 | 20 mM Histidine, 20 mM Methionine, 4% Sucrose, 0.2% Polysorbate-80, pH 6.0 | 127 | 50.95 | Not Done |
| MYO-029 | 20 mM Histidine, 20 mM Methionine, 4% Sucrose, 0.2% Polysorbate-80, pH 6.0 | 167 | 71.52 | Not Done |

The data shown in Table 1 demonstrate that the viscosity of anti-myostatin (MYO-029) is significantly higher compared to the other antibodies listed in the Table. The viscosities of all of the antibodies increased at 4° C. This increase is proportionally much higher for MYO-029.

Example 2

Effect of Various Salts on the Viscosity of an MYO-029 Antibody Formulation

MYO-029 antibody, at a concentration of 73 mg/ml, was formulated in 10 mM histidine, 2% sucrose, pH 6.0. Concentrated solutions of salts (e.g. calcium chloride, magnesium chloride, sodium chloride, and sodium biphosphate) were diluted into the MYO-029 antibody formulation using a pipette. The effect of these salts on the viscosity of MYO-029 antibody formulation was measured as described in Example 1. These data are shown in FIG. 1.

Both $MgCl_2$ and $CaCl_2$ at concentrations ranging from about 5 mM to about 20 mM significantly reduced the viscosity of the MYO-029 antibody formulation. NaCl and $NaH_2PO_4$, on the other hand, had little effect in this range.

Thus, calcium chloride and magnesium chloride, at concentrations of about 5 mM to about 20 mM, are effective viscosity reducing agents for MYO-029 antibody formulations, unlike sodium chloride and sodium biphosphate.

Example 3

Effect of Calcium Chloride on the Viscosity of a J695 Antibody Formulation

The viscosity of a J695 antibody formulation is measured at two different J695 antibody concentrations, i.e., 100 mg/ml and 300 mg/ml.

The viscosity of the J695 antibody formulation at the higher concentration will be higher than the viscosity of the J695 antibody formulation at the lower concentration.

Calcium chloride is added to a final concentration of about 5 mm, to 20 mM to the 300 mg/ml J695 antibody formulation. In this case the viscosity of the antibody formulation is expected to decrease compared to the J695 formulation without calcium chloride.

Accordingly, calcium chloride, at concentrations of about 5 mM to about 20 mM, is effective as a viscosity reducing agent for J695 antibody formulations.

Example 4

Effect of Calcium Chloride on the Viscosity of a MYO-028 Antibody Formulation

MYO-028, another anti-myostatin antibody, was concentrated using Centricon Ultrafree®-4 to a concentration of 95 mg/mL. Calcium chloride was added to MYO-028 according to Table 2 below:

TABLE 2

| $CaCl_2$ Conc. | MYO-028 (μL) | $CaCl_2$ Solution (μL) | Buffer (μL) |
|---|---|---|---|
| 0 mM | 316.9 | 0 | 8.125 |
| 25 mM | 316.9 | 4.06 | 4.06 |
| 50 mM | 316.9 | 8.125 | 0 |

MYO-028 was formulated at 95 mg/mL in 10 mM histidine, 5% sucrose, pH 6.5. The $CaCl_2$ solution consisted of 10 mM histidine, 2% sucrose, 2M $CaCl_2$. The buffer solution consisted of 10 mM histidine, 5% sucrose, pH 6.5.

The viscosity of these MYO-028 antibody formulations was measured using the same rheometer method as described in Example 1 with the additional use of a solvent trap to prevent evaporation, a 100 μL liquid sample load of MYO-028 on the plate, and the test was performed at room temperature.

Figure 2:
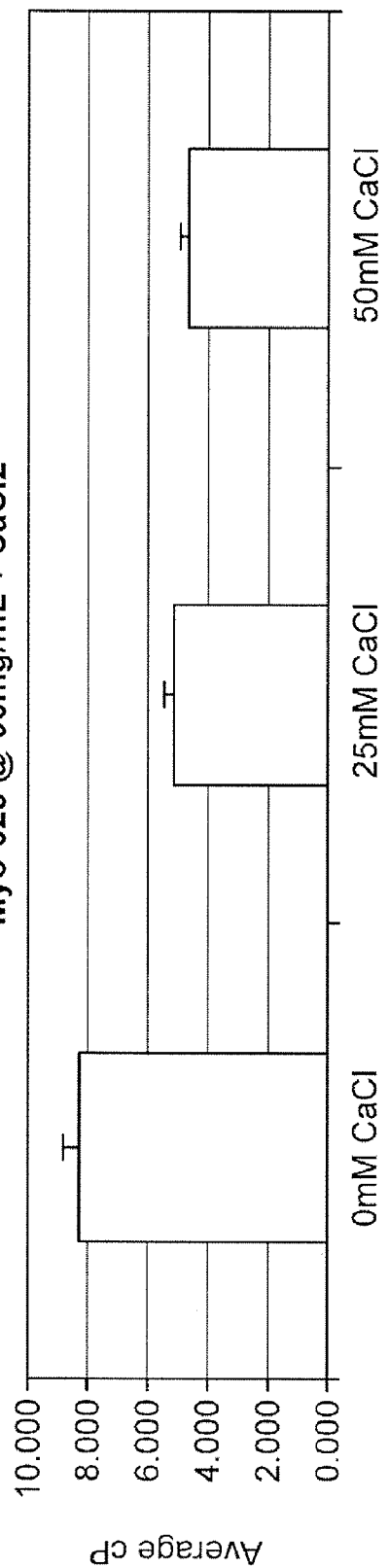
FIG. 2 is a bar graph depicting the results of experiments conducted to determine the effect of increasing concentrations of calcium chloride on the viscosity of an anti-myostatin (MYO-028) antibody formulation.

The data from these experiments are shown in FIG. 2.

The addition of $CaCl_2$ decreased the viscosity of a MYO-028 antibody formulation at 25 mM and 50 mM $CaCl_2$ compared to a MYO-028 formulation lacking $CaCl_2$. These data demonstrate the suitability of $CaCl_2$ for use as an agent to reduce viscosity of a protein formulation, e.g., to formulate a reduced viscosity antibody formulation.

Example 5

Effect of Calcium Chloride on the Viscosity of a IMA-638 Antibody Formulation

To test the effect of calcium chloride on the viscosity of an IMA-638 antibody formulation, different amounts of calcium chloride were added with a pipette to aliquots of the IL-13 antibody, IMA-638. The IMA-638 antibody aliquots had a protein concentration of approximately 150 mg/mL. FIG. 3 provides a graphical depiction of the effect of calcium chloride on the viscosity of IMA-638 protein formulations.

The viscosity of the IMA-638 did not show the same reduction in viscosity as observed for MYO-029. These data demonstrate a method of identifying a suitable viscosity reducing agent for use with a protein formulation.

Example 6

Effect of Calcium Chloride on the Stability of MYO-029 Antibody

Addition of a compound (i.e., a viscosity reducing agent, e.g., $CaCl_2$) to a protein formulation could potentially affect the molecules' stability towards freeze-thaw-induced stresses. This effect could either be detrimental, beneficial, or have no effect on a proteins' stability during freezing and thawing.

To evaluate the effect of an agent (i.e., $CaCl_2$) on the freeze-thaw-induced degradation of MYO-029 antibody, the molecule was subjected to 10 freeze thaw cycles at −80° C. and 37° C., in the presence or absence of 5 mM $CaCl_2$. MYO-029 drug substance was formulated into 10 mM histidine, 2% sucrose, in the presence or absence of calcium chloride by ultrafiltration and diafiltration. The final protein concentration was approximately 75 mg/mL. Twenty microliter aliquots were frozen at −80° C. and thawed at room temperature. This was repeated for 5 and 10 freeze-thaw cycles. Samples were diluted 25-fold with formulation buffer and analyzed by measuring absorbance at 280 nm for protein concentration and SEC-HPLC for the percentage of high molecular weight products (% HMW).

The effect of freeze-thaw-induced degradation was assessed by (i) protein recovery (absorbance at 280 nm), and (ii) percentage of high molecular weight (% HMW) formation as determined by size exclusion-high performance liquid chromatography (SEC-HPLC). HMW formation is the most common degradation pathway for this molecule. The results of these studies are shown in FIG. 4A and FIG. 4B.

Compared to the corresponding control sample without $CaCl_2$, addition of 5 mM $CaCl_2$ to the formulation did not have any effect on protein recovery or % HMW formation. Thus, the addition of calcium chloride does not appear to impact the stability of MYO-029 antibody formulations. This indicates that suitability of $CaCl_2$ for use as a viscosity reducing agent in a protein formulation, e.g., in a reduced viscosity antibody formulation.

Example 7

Effect of Calcium Chloride on the Stability of a MYO-029 Antibody Formulation

Addition of $CaCl_2$ to a protein formulation could potentially affect the molecules' liquid stability over time. This effect could either be detrimental, beneficial, or have no effect on the proteins' stability during storage.

To evaluate the effect of this agent on the liquid stability of MYO-029 on heat-induced degradation, formulations containing MYO-029 were subjected to storage at 50° C. for up to seven days. Aliquots were taken at various time points and analyzed for protein concentration by absorbance at 280 nm and % HMW was analyzed by SEC-HPLC. The data are shown in FIG. 5A and FIG. 5B.

Compared to the control sample, addition of $CaCl_2$ to the formulation had no negative effect on the stability of the protein in the liquid state stored at 50° C. The percentage of HMW in the drug substance also appeared to be slightly less in the material containing $CaCl_2$. These data further demonstrate the suitability of using $CaCl_2$ as a viscosity reducing agent. They also demonstrate a method of determining the suitability of an agent that reduces viscosity of a protein formulation, e.g., with respect to whether the agent has an effect on stability of protein in the formulation.

Example 8

Effect of Calcium Chloride on the Stability of Lyophilized MYO-029

Addition of an agent such as $CaCl_2$ to a protein formulation could potentially affect the proteins' lyophilized dosage forms stability over time. This effect could be either detrimental, beneficial or have no effect on the proteins' stability during storage.

To evaluate the effect of this excipient on the stability of lyophilized MYO-029, a formulation containing the molecule is lyophilized both with and without (control) 5 mM $CaCl_2$ and is subject to storage at 50° C. and 4° C. for four weeks. Vials are pulled weekly and analyzed for protein concentration by absorbance at 280 nm, percentage of HMW by SEC-HPLC, and charge distribution by cation exchange-high performance liquid chromatography (CEX-HPLC). Vial withdrawal volume and viscosity (one time-point only) are also measured.

A. Viscosity of Reconstituted Drug Product

The viscosity of the MYO-029 drug product (which is measured in substantially the same manner as in Example 1) at approximately 150 mg/mL is reduced when 5 mM calcium chloride is present in the formulation.

B. Withdrawal Volume from the Vial

The amount of drug product that can be removed from the vial with a 1 mL syringe and 21 G needle is improved when $CaCl_2$ is present in the formulation.

C. Protein Concentration

Compared to the control, addition of $CaCl_2$ to the formulation does not affect protein recovery.

D. High Molecular Weight

Five mM $CaCl_2$ will not have any significant effect on the percentage of HMW species that is formed after four weeks of storage at 4° C. However, at 50° C., the rate of HMW formation is expected to be significantly reduced compared to the control.

E. Charge Distribution

The stability time-points are analyzed by CEX-HPLC, a chromatographic tool used to study charge differences in proteins. In CEX-HPLC, the more negatively charged molecules elute earlier than the more positively charged molecules. This method is used to detect deamidation of asparagines residues to either aspartic or iso-aspartic acid. Deamidation results in an increase in the proteins' net negative charge, and it will elute earlier from the HPLC column. In this experiment, the effect of calcium chloride has on protein degradation resulting in a charge change different from that of the control is investigated. Compared to the control without calcium chloride, the same charge changes are expected to occur over time. Thus, $CaCl_2$ is expected to have no effect on the charge distribution of MYO-029 at both storage temperatures.

In summary, compared to a control sample, addition of $CaCl_2$ to a formulation will have no significant negative effect on the stability of the protein in the formulation relative to the no calcium chloride experimental control in the lyophilized state when stored at 4° C. and 50° C. In some instances, $CaCl_2$ is found to be beneficial to the stability of the protein.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A reduced viscosity formulation, comprising:
   (i) an antibody or an antigen binding fragment thereof;
   (ii) magnesium chloride at a concentration of between about 0.5 mM and about 25 mM in the formulation; and
   (iii) a buffer;
   wherein the pH of the formulation is about 5.5 to about 6.5.

2. The reduced viscosity formulation of claim 1, further comprises at least one of an antioxidant, a surfactant, and a cryoprotectant.

3. The reduced viscosity formulation of claim 1, wherein the antibody is an anti-myostatin antibody.

4. The reduced viscosity formulation of claim 3, wherein the anti-myostatin antibody is MYO-022, MYO-028, or MYO-029.

5. The reduced viscosity formulation of claim 1, wherein the antibody is an anti-IL-12 antibody.

6. The reduced viscosity formulation of claim 5, wherein the anti-IL-12 antibody is J695.

7. The reduced viscosity formulation of claim 1, wherein the antibody is an anti-IL-13 antibody.

8. The reduced viscosity formulation of claim 7, wherein the anti-IL-13 antibody is IMA-638.

9. The reduced viscosity formulation of claim 1, wherein magnesium chloride is at a concentration of about 1 mM in the formulation.

10. The reduced viscosity formulation of claim 1, wherein the magnesium chloride is at a concentration of about 2.5 mM in the formulation.

11. The reduced viscosity formulation of claim 1, wherein the magnesium chloride is at a concentration of about 5 mM in the formulation.

12. The reduced viscosity formulation of claim 1, wherein the magnesium chloride is at a concentration of about 10 mM in the formulation.

13. The reduced viscosity formulation of claim 1, wherein the magnesium chloride is at a concentration of about 15 mM in the formulation.

14. The reduced viscosity formulation of claim 1, wherein the magnesium chloride is at a concentration of about 20 mM in the formulation.

15. The reduced viscosity formulation of claim 1, wherein the magnesium chloride is at a concentration of about 25 mM in the formulation.

16. The reduced viscosity formulation of claim 1, wherein the buffer is histidine buffer.

17. The reduced viscosity formulation of claim 16, wherein the histidine buffer is at a concentration of about 4 mM: to about 60 mM.

18. The reduced viscosity formulation of claim 1, wherein the pH of the formulation is 6.0.

19. A reduced viscosity formulation, comprising:
(i) an antibody or an antigen binding fragment thereof, wherein the antibody is selected from the group consisting of an anti-myostatin antibody, an IL-12 antibody, an IL-13 antibody, and a combination thereof;
(ii) a viscosity reducing agent at a concentration of between about 0.5 mM and about 25 mM in the formulation, wherein the viscosity reducing agent is calcium chloride or magnesium chloride; and
(iii) a buffer;
wherein the pH of the reduced viscosity formulation is about 5.5 to about 6.5.

* * * * *